United States Patent [19]

Smith

[11] 4,381,151
[45] Apr. 26, 1983

[54] HAND-HOLDABLE CONTAMINATION TESTER

[75] Inventor: Tennyson Smith, Thousand Oaks, Calif.

[73] Assignee: The United States of America as represented by the Secretary of the Air Force, Washington, D.C.

[21] Appl. No.: 200,225

[22] Filed: Oct. 23, 1980

[51] Int. Cl.³ ............................................. G01N 21/21
[52] U.S. Cl. ..................................... 356/369; 356/364
[58] Field of Search ............................... 356/364–365, 356/369, 370, 446, 448; 250/225

[56] References Cited

U.S. PATENT DOCUMENTS

| | | | |
|---|---|---|---|
| 1,756,785 | 4/1930 | Gallasch | 356/448 |
| 2,415,436 | 2/1947 | Maris | 356/33 |
| 3,718,399 | 2/1973 | Kalman | 356/448 |
| 3,721,500 | 3/1973 | Fugitt | 356/369 |
| 3,874,797 | 4/1975 | Kasai | 356/369 |

OTHER PUBLICATIONS

Bockeris et al., "The Anodic Formation of Calomel Films on Mercury Electrodes-an Ellipsometric-Galvanostatic Study" Proc. Roy. Soc. (London) 1964, pp. 345-377.

Gottesfeld et al., "The Monitoring of Fast Changes in the Optical Properties of Electrode Surfaces with a Classical Ellipsometer", Surface Science, 44, 1974, pp. 377-388.

Smith, T. "NDT Techniques for the Prediction of Adhesive Failure Loci Prior to Bonding" Materials Evaluation, 33, 5-1975, pp. 101-106.

Sivertsen et al., "A Field Instrument for Water Vapour Measurements" Infrared Physics 15, & 5-1975, pp. 79-82.

Primary Examiner—William H. Punter
Attorney, Agent, or Firm—Donald J. Singer; Jacob N. Erlich

[57] ABSTRACT

A hand-holdable apparatus for testing, and a method of testing, a light-reflective surface for contamination. The apparatus and the method are based upon a novel "off null" ellipsometry technique by the use of which contamination of the surface is ascertained, if the intensity of light reflected by the surface being tested exceeds a predetermined threshold of intensity.

2 Claims, 3 Drawing Figures

4,381,151

HAND-HOLDABLE CONTAMINATION TESTER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to the detection of contamination and, more particularly, to an apparatus for and a method of testing a light-reflective surface for contamination.

There is a current need in the art for a surface tool that can detect contamination on a light-reflective surface (such as those of metals) prior to painting, adhesive bonding, and the like. It has been already demonstrated in the art that ellipsometry is excellent for this purpose, and an automated contaminated mapping system has been proved feasible. The automated system is ideal for facilities with large numbers of identical parts, but not for those facilities with a small number of parts with various sizes and shapes. A portable, small (i.e., about the size of a two-cell flashlight), hand-holdable contamination tester is not only desirable, but also is necessary, in this situation (i.e., the inspection of a small number of parts of various sizes and shapes).

I have fulfilled this current need by inventing a hand-holdable contamination tester for inspecting a light-reflective surface, and a related method for testing such a surface for contamination.

By my invention I have significantly advanced the state-of-the-art.

SUMMARY OF THE INVENTION

My invention is a unique apparatus for, and a novel method of, quickly, easily, reliably, and accurately testing a light-reflective surface for contamination. Both are based on my "off null" ellipsometry technique, which will be explained in detail later herein, by the use of which contamination of the surface is ascertained if the intensity of light reflected by the surface being tested exceeds a predetermined threshold of intensity.

Accordingly, an object of this invention is to provide an apparatus for detecting contamination on the light-reflective surface of an item.

Another object is to provide a tester for detecting contamination on the light-reflective surface of a metal item.

Still another object is to provide a tester for detecting contamination on the light-reflective surface of the tested item in a quick and accurate manner.

Yet another object is to provide such a tester as hereinbefore described that is simple in structure.

A further object is to provide such a tester that is easy to manufacture and that can be made at low cost.

A still further object is to provide such a tester that is simple to use and economical to operate.

A yet further object is to provide such a tester that is portable, i.e., can be easily carried and used by one individual.

A yet still further object is to provide such a tester that is hand-holdable, and that is useable while hand-held.

Another still further object of this invention is to teach the fundamental steps of a novel method of testing a light-reflecting surface for contamination.

Still another object of this invention is to teach my "off null" ellipsometry technique, both generally and also as adapted for use with my apparatus and with my method.

These objects, as well as related objects, of this invention will become readily apparent after a consideration of the description of the invention, together with reference to the contents of the Figures of the drawing.

DETAILED DESCRIPTION OF THE PREFERRED EMBODIMENT

Figure 1:
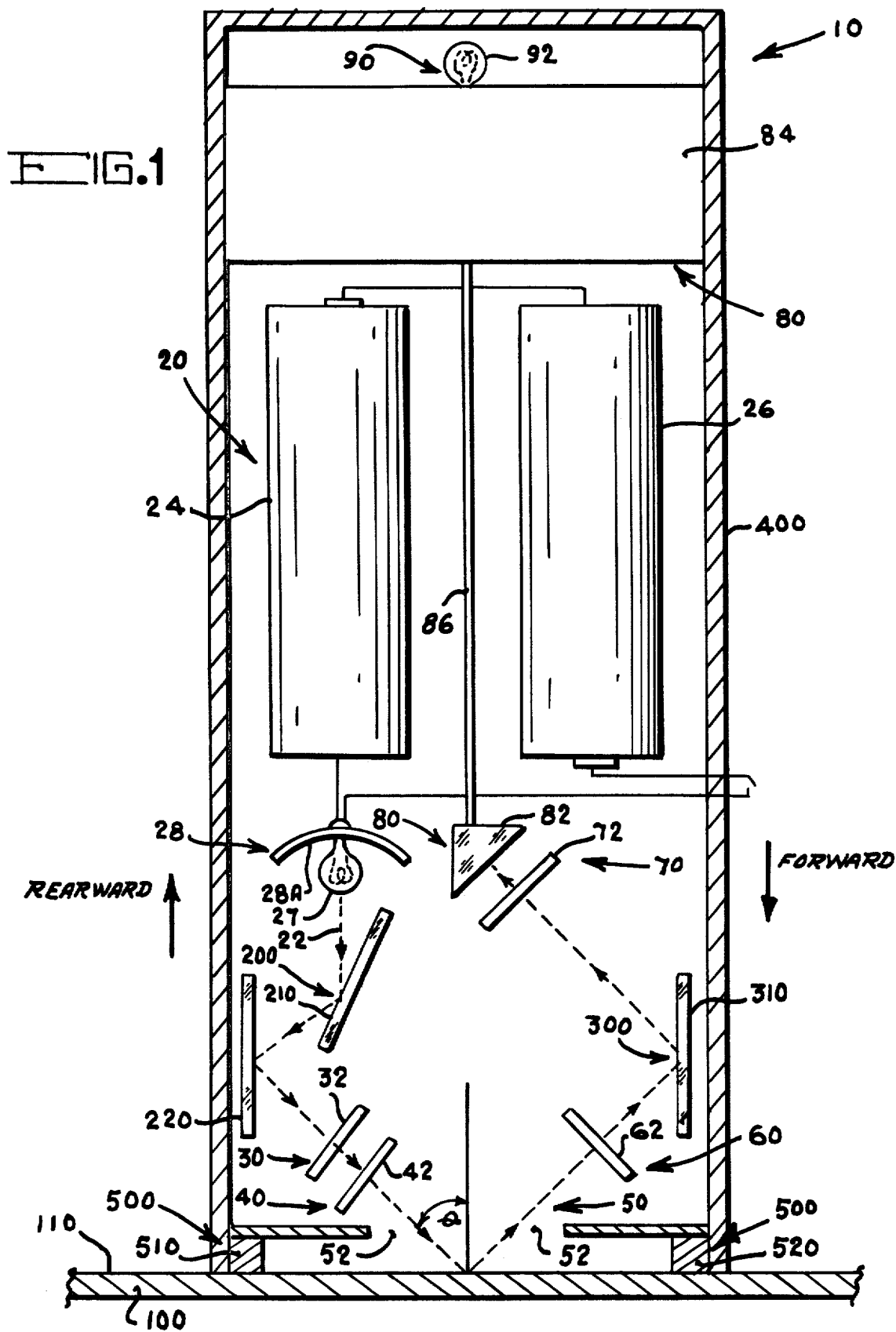
FIG. 1 is a top view, in simplified schematic and pictorial form, and partially in cross section, of a preferred embodiment of the inventive hand-holdable contamination tester, shown in an enlarged size in the interest of maintaining clarity of components thereof and of showing their respective positional relationships.

With reference to FIG. 1, therein is shown a preferred embodiment 10 of my inventive hand-holdable contamination tester. It is to be remembered that the tester 10 is shown in FIG. 1 in an enlarged size to promote clarity of the components and their respective positional relationship, and to avoid encumbrance of the FIGURE. The preferred top view dimensions (i.e., length, width, but not depth) are two (2) inches by five (5) inches.

In the most basic and generic structural form, the tester 10 comprises the following components: (a) means, generally designated 20, for emitting a beam of light 22; (b) means, generally designated 30, for plane polarizing the beam of light 22, with this means 30 disposed in optical alignment with the light beam emitting means 20; (c) compensator means 40 that is disposed in optical alignment with the light beam plane polarizing means 30; (d) means, generally designated 50, for causing the plane polarized, compensated, emitted beam of light 22 to impinge at a predetermined angle of incidence $\theta$ upon the light-reflective surface 110 of a specimen 100 that is being tested for contamination, with this means 50 disposed in optical alignment with the compensator means 40; (e) analyzer means 60 disposed in optical alignment with the light impingement causing means 50; (f) means 70 for permitting the transmission of only a preselected constituent wavelength of the beam of light 22, with the transmitted light having an intensity I, and with this mean 70 disposed in optical alignment with the analyzer means 60; (g) means, generally designated 80, for detecting the beam of light 22 and for measuring the intensity I of the beam of light 22 that is transmitted by the light transmission means 70, with this means 80 disposed in optical alignment with the light transmission means 70; and, (h) means, generally designated 90, for indicating if the intensity I of the detected light exceeds a predetermined threshold of intensity of light, with this means 90 operatively associated with the light detecting means 80.

It is here to be noted and to be remembered that, if a second component is in optical alignment with a first component, the specific (as distinguished from the general) physical location of the second component relative to the first component is not definitely ascertained (i.e., it may be physically forward of, or rearward of, or above, or below, and the like, relative to the first component). Accordingly, and as indicated by the "Forward" and "Rearward" designations in FIG. 1, as a matter of preference, the plane polarizing means 30 is disposed physically forward of the light emitting means 20; the compensator means 40 is disposed physically forward of the plane polarizing means 30; the light impingement causing means 50 is disposed physically forward of the compensator means 40; the analyzer means 60 is disposed physically forward of the light transmission means 70, and physically rearward of the light impingement causing means 50; and, the light transmission means 70 is disposed physically forward of the light detecting means 80.

Also as a matter of preference, and not of limitation, the plane polarizing means 30 includes a Glan-Thompson prism 32; the compensator means 40 includes a quarter-wave plate 42; the analyzer means 60 includes a Glan-Thompson prism 62; the light transmission means 70 includes a monochromatic filter 72; and the light detecting means 80 includes a photodetector 82 which is in electrical connection with its electronic control 84 by way of an interconnecting electrical conductor 86.

Also as a matter of preference, my inventive contamination tester 10, FIG. 1, further comprises additional components for reducing or shortening the geometric distance (i.e., the linear distance, or "displacement" in a front-to-rear direction, or vice versa, of the tester) travelled by the light beam (i.e., the optical path). This geometric shortening of the optical path results in a "folding" of the optical path, so that the geometric distance actually travelled is significantly less than the length of the optical path. In this regard, and with reference to FIG. 1 and to the additional components preferred, these components are: means (generally designated 200), in optical alignment with the emitted beam of light 22 and physically disposed between the plane polarizing means 30 the light beam emitting means 20, for shortening the geometric distance (as described hereinabove) of the optical path between these two means 20 and 30; and, means (generally designated 300), in optical alignment with the analyzer means 60 and physically disposed between the analyzer means 60 and the light transmission means 70, for shortening the geometric distance (as described hereinabove) of the optical path between these two means 60 and 70. It is here to be noted that means 200 and means 300 also function to align (or direct) the emitted light beam 22.

Still with reference to FIG. 1, and still with reference to means 200 and means 300, the means 200 preferably includes a first mirror 210 and a second mirror 220 that are physically disposed between the light beam emitting means 20 and the plane polarizing means 30, such that the emitted light beam 32 impinges upon the first mirror 210, is reflected from the first mirror 210 to the second mirror 220, and is further reflected from the second mirror 220 to the analyzer means 30. Likewise, means 300 includes a third mirror 310 that is physically disposed between the analyzer means 60 and the light transmission means 70, such that the beam of light 22 that is transmitted by the analyzer means 60 impinges upon the third mirror 310 and is reflected from the third mirror 310 to the light transmission means 70.

As can be seen from FIG. 1 which is an enlarged and oversized depiction of the inventive tester 10, the components of the tester (i.e., 20, 200, 30, 40, 50, 60, 300, 70 80 and 90) are dimensional, configurated, physically and optically disposed, and housed in a common container 400 such that the tester obviously is portable (i.e., can be easily carried and used by one individual). It is to be remembered, however, that the preferred width and length dimensions of the common container are approximately two (2) inches by five (5) inches, such that the tester is hand-holdable and useable while hand-held.

With reference to FIG. 1, it is to be noted that the tester further comprises means (generally designated 500), disposed external of the common container 400 and adjacent to the light beam impingement causing means 50, for abutting the light-reflective surface 110 and for permitting a spaced apart relationship between the common container 400 and the light reflective surface 110. This means 500 includes, as a matter of preference, a pair (i.e., two) feet member 510 and 520 that are spaced apart, and preferably are disposed such that one foot is positioned at one of the two forward corners of the common container 400, and the other foot is disposed at the other forward corner of the common carrier 400.

It is here to be noted that the light beam impingement causing means 50 includes an opening 52 (or window) in the common container 400 between the spaced-apart pair of feet members 510 and 520.

It is also to be noted that the light beam emitting means 20, as shown in FIG. 1, includes: a source of electrical power, such as electrical batteries 24 and 26; a light bulb 27 in electrical connection with the source of electrical power 24 and 26, with the bulb 27 emitting light; and, means 28 for collimating the emitted light, such that the beam of light 22 is formed. The collimating mean 28 preferably includes, as shown in FIG. 1, a concave reflector 28A that is disposed physically rearward of the light bulb 27.

It is further to be noted that, as shown in FIG. 1, the means 90, for indicating if the intensity of the detected light 22 exceeds a predetermined threshold of intensity of light, includes a visual indicating means, such as light bulb 92 which is in electrical connection with the electronic control 84 of photodetector 82 of means 80.

MANNER OF OPERATION AND OF USE OF THE PREFERRED EMBODIMENT

As preliminary matters, it is to be noted: that, prior to use, the tester 10, FIG. 1 must be calibrated; and, that the structure and use of the tester 10 is based on my "off null" ellipsometry technique, which will be explained later herein.

To calibrate the tester, a specimen (not shown) which is made of the same preselected material as the specimen to be tested (i.e., specimen 100, FIG. 1), and which has an uncontaminated light-reflective surface, is used as a control sample. The feet 510 and 520 of the tester 10 are placed or abutted against the uncontaminated, light-reflective surface of the control sample. Then, the polarizer means 30, the compensator means 40, and the analyzer means 60 are adjusted until a light "null" is reached (i.e., the "readout" or "warning" light bulb 92 dims to a minimum). Next, the light-reflective, uncontaminated surface of the control sample is moved, re-oriented, and the like (while still being tested by the tester 10), and the gain on the photodetector 82 as shown on the electronic control 84 is adjusted such that light bulb 92 does not light up for any position of the uncontaminated, light-reflective surface of the control sample. The tester 10 is now calibrated and is ready for use to test the light-reflective surface 110 of the specimen 100 for contamination.

To use the calibrated tester 10, all that need be done is to position the feet 510 and 520 of the tester 10 in abutting contact against the light-reflective surface 110 of the specimen 100. Then, if the light bulb 92 lights up, the surface 110 is contaminated. Conversely, if the light bulb 92 does not light up, the surface 110 is not contaminated.

In using the tester 10 to determine if the light-reflective surface 110 of specimen 100 is contaminated, what occurs sequentially is more specifically as follows. The emitted beam of light 22: impinges upon and is reflected first and second mirrors 210 and 220; passes through polarizer means 30, and thereby is plane polarized (i.e., sometimes referred to as "linearly polarized"); passes through compensator means 40; passes through the window 52 of the common container 400; impinges upon, and is reflected from, the light-reflective surface 110 of the specimen 100 being tested; passes through the analyzer means 60; impinges upon and is reflected by the third mirror 310; passes through monochromatic filter 72 of the light transmission means 70, and thereby results in monochromatic beam of light; impinges upon the photodetector 82; and, energizes (i.e., lights up) light bulb 92, in direct proportion to the intensity of the light that strikes the photodetector 82.

Figure 2:
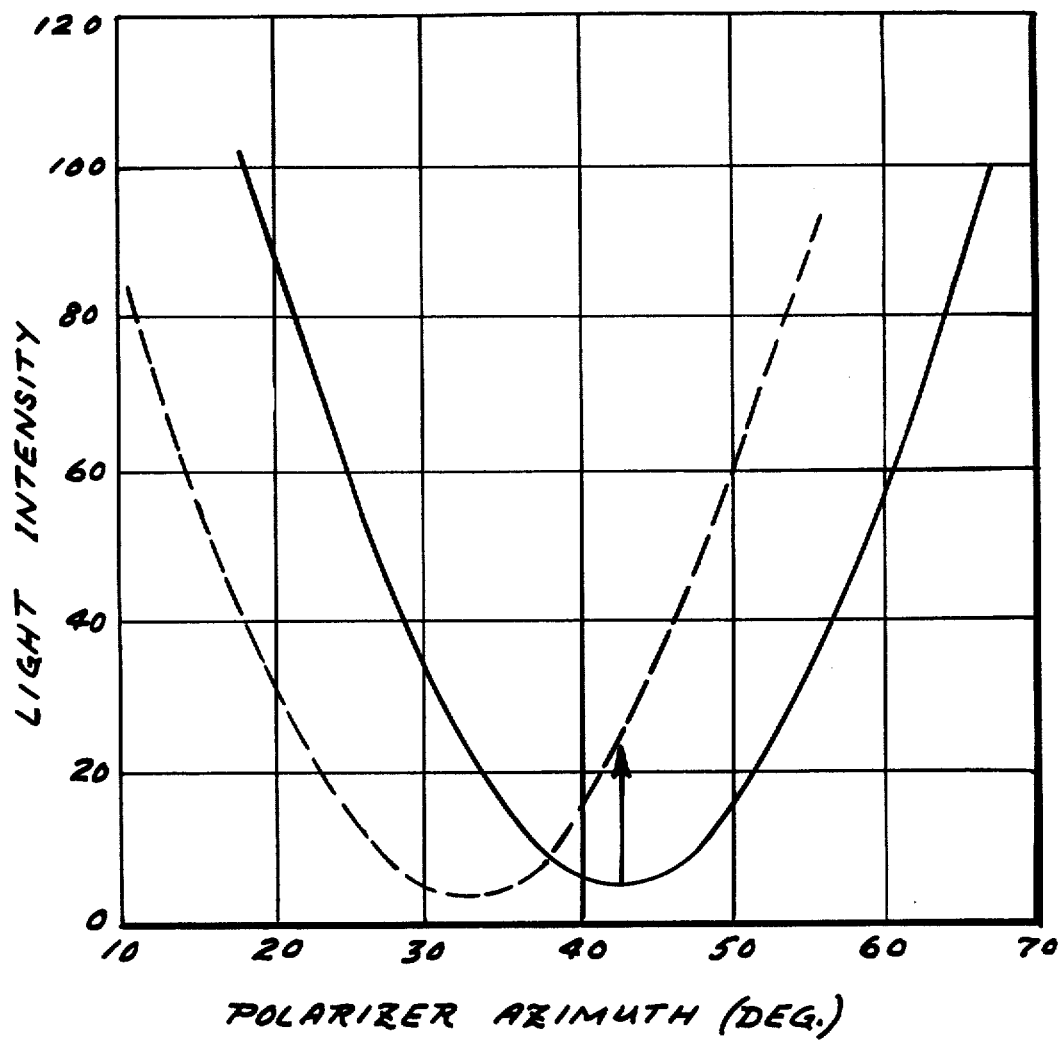
FIG. 2 is a plot, in graph form, of light intensity as compared to polarizer azimuth for the reflection of red light ($\lambda = 6238$ Å) from a representative specimen having a light-reflective surface (i.e., an aluminum panel)
Figure 3:
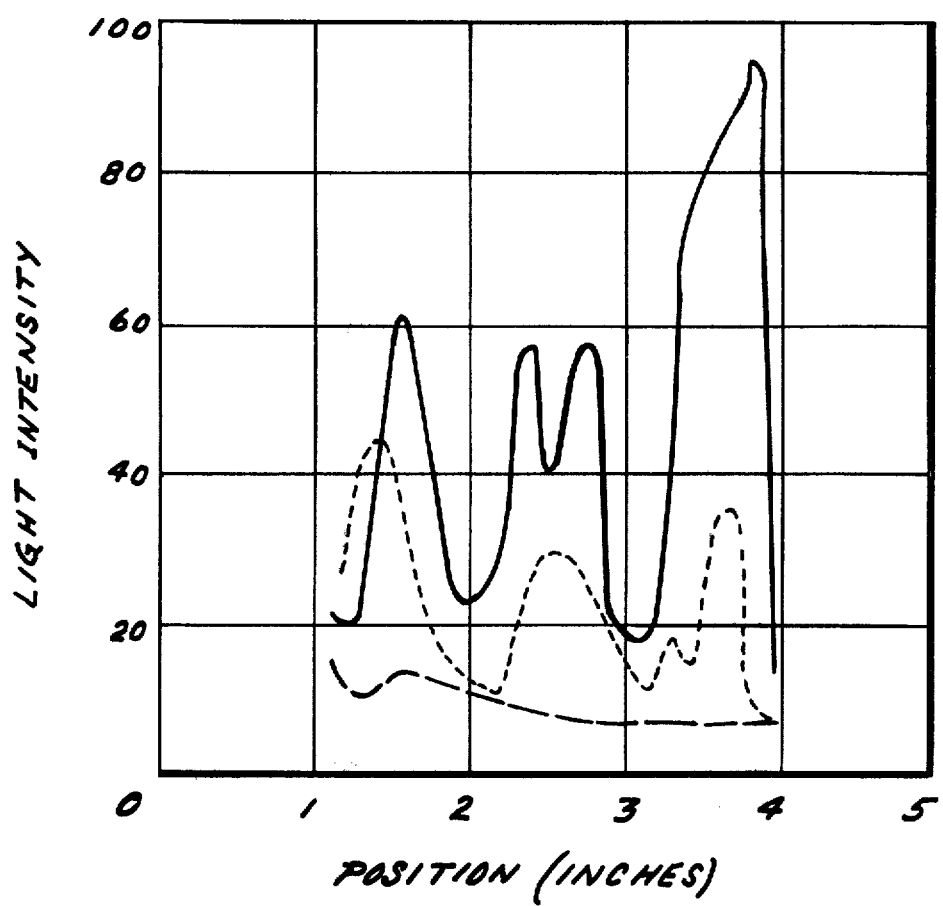
FIG. 3 also is a plot, in graph form, of light intensity as compared to position (i.e., distance) on the representative specimen.

Why my tester 10 functions as it does is best explained by describing my "off null" ellipsometry technique with the help of the contents of FIGS. 2 and 3, to which reference is now made. FIG. 2 is a plot of light intensity verses polarizer azimuth for reflection of red light ($\lambda = 6328$ Å) from an aluminum panel which, of course, has a light-reflective surface. For conventional ellipsometry the intensity minimum (i.e., "null") is used to obtain the polarizer azimuth which relates to the surface optical properties. If the optical properties change, the polarizer is rotated to a new null. However, in my "off null" ellipsometry technique, the polarizer (such as 32, FIG. 1) is set at null and the optical changes are noted by the change in light intensity I. For example, and still with reference to FIG. 2, the null position for the aluminum plate referred to hereinbefore (as represented by the solid line curve in FIG. 2) is $P=43.5°$. The addition of a contamination film (i.e., a layer of contamination) to the light-reflective surface of the aluminum panel shifts the null position (as represented by the dashed line curve in FIG. 2) to $P=33.5°$. If the polarizer is left at 43.5°, the intensity I of the light increases from approximately 4 to approximately 20, as indicated by the arrow in FIG. 2.

The advantages of using my "off null" technique are increased sensitivity, and the fact that optical changes can be followed without mechanical motion of the ellipsometer parts. These advantages, or properties, are ideal for the rapid scanning of a geometrical area or for rapid following of changes with time. To illustrate sensitivity, reference is made to FIG. 3 which shows plots of intensity I as compared to position (i.e., 1 to 4 inches) on an aluminum panel. The lower dashed curve is the intensity profile for the uncontaminated surface; the dotted curve is for brassidic acid contamination between positions 1 and 2, 2 and 3, and 3 and 4; and, the solid line is for contamination with erucic acid. Any area of this panel where the intensity I is less than 20 is considered acceptable (i.e., not contaminated), and any area where the intensity I is greater than 20 would be considered contaminated and unacceptable.

DESCRIPTION OF THE INVENTIVE METHOD

As a preliminary matter, reference is made to FIGS. 2 and 3 which show the genesis of my inventive method, and to FIG. 1 which shows the result of practicing the steps of my method.

My method of testing a light-reflecting surface (such as surface 110, FIG. 1) of a preselected material for contamination comprises, essentially, the following steps.

Firstly, impinging a beam of light (such as 22, FIG. 1) upon a uncontaminated light-reflective surface of a first specimen (not shown) of preselected material, whereby the light beam is reflected from the uncontaminated light-reflective surface with an intensity.

Next, measuring the intensity of the reflected light.

Then, impinging the same beam of light upon a light-reflective surface (such as 110, FIG. 1) of a second specimen (such as 100, FIG. 1) that is made of the same preselected material as the first specimen, wherein the light-reflecting surface of this second specimen is being tested for contamination, thereby the impinging light beam is reflected from the light-reflecting surface with an intensity.

Next, measuring the intensity of the light reflected by the light-reflective surface of this second specimen.

Lastly, comparing the measured intensity of the light beam reflected from the uncontaminated light-reflective surface of the first specimen with the measured intensity of the light beam reflected from the light-reflective surface of the second specimen.

It is here to be noted that, if the measured intensity of the light beam reflected from the light-reflective surface of the second specimen exceeds the measured intensity of the light beam reflected from the uncontaminated light-reflective surface of the first specimen (i.e., the "control" specimen), then the light-reflective surface of the second specimen is contaminated.

CONCLUSION

It is abundantly clear from all of the foregoing, and from the Figures of the drawings, that the stated objects of the invention, as well as related objects of the invention, have been achieved.

It is here to be noted that, although there have been described and shown the fundamental and unique features of my invention as applied to a preferred embodiment, various other embodiments, variations, adaptations, substitutions, additions, omissions, and the like, may occur to, and can be made by, those of ordinary skill in the art, without departing from the spirit of my invention. For example:

(a) The source of electrical power need not be batteries, such as 24 and 26, FIG. 1, but can be an extension cord in electrical connection at one end to light bulb 92, and at the other end to a standard electrical outlet or other source of electrical power such as a generator.

(b) The means for emitting a beam of light 20, FIG. 1, may include a laser, rather than a light bulb 27 and a collimater 28A.

(c) The light intensity indicating means 90 may comprise an audible indicating means, rather than the visual indicating means shown in FIG. 1 (i.e., the light bulb 92).

(d) The tester 10, FIG. 1, may be provided with two extendable legs, rather than the two legs 510 and 520 that are of a preselected length, so that if the light-reflective surface of a test item cannot be reached by both legs of the same length, then one leg may be extended.

(e) If the light-reflective surface of the test item should not (or cannot) be touched for any one of many reasons, then the tester can be provided with an auxiliary alignment light bulb. In that event, the schematic top view in cross section of the auxiliary light bulb, the mirrors, and the light path would be similar to the arrangement in FIG. 1, but with the tester rotated 90° about its vertical axis. An iris would be placed in the path of the light beam, such that a maximum intensity strikes the photodetector 82 if the tester 10 has the proper orientation.

(f) The tester 10 can, of course, be provided with a switch means, as shown in FIG. 1, so that the source of electrical power 20 selectively may be turned on and off.

(g) the tester, FIG. 1, may be provided with a leg in addition to legs 510 and 520, so that it can be balanced on any planar surface, and the three legs may be extendable.

Additionally, because of my teaching, it may occur to others of ordinary skill in the art that, in appropriate particular circumstances, the number of the basic and fundamental steps of my inventive method can be increased or otherwise varied, and/or that their sequence can be changed. In this regard, it is to be noted that the same desired results that I obtain will be obtained, irrespective of any variation of the steps of my method.

What is claimed is:

1. A hand-holdable contamination tester, comprising:
   a. means for emitting a beam of light, wherein this means includes: a source of electrical power; a light bulb in electrical connection with said source of electrical power, with said bulb emitting light; and means for collimating said emitted light, such that a beam of light is formed, wherein this means includes a concave reflector disposed physically rearward of said light bulb;
   b. means for plane polarizing said beam of light, wherein this means is disposed in optical alignment with and physically forward of said light beam emitting means, and wherein this means includes a Glan-Thompson prism;
   c. means, in optical alignment with said emitted beam of light and physically disposed between said means for emitting a beam of light and said means for plane polarizing said beam of light, for shortening the geometric distance of an optical path between said light emitting means and said plane polarizing means, wherein this means for shortening said geometric distance includes a first mirror and a second mirror physically disposed between said light emitting means and said plane polarizing means, such that said emitted light beam impinges upon said first mirror, is reflected therefrom to said second mirror, and is further reflected therefrom to said polarizing means;
   d. compensator means disposed in optical alignment with and physically forward of said means for plane polarizing said beam of light, wherein said compensator means includes a quarter-wave plate;
   e. means for causing said plane polarized, compensated, emitted beam of light to impinge at a predetermined angle of incidence upon a light-reflective surface which is being tested for contamination, with this means disposed in optical alignment with and physically forward of said compensator means;
   f. analyzer means disposed in optical alignment with and physically rearward of said light impingement causing means, wherein said analyzer means includes a Glan-Thompson prism;
   g. means for permitting transmission of only a preselected constituent wavelength of said beam of light, with the light transmitted having an intensity, wherein this means includes a monochromatic filter, and wherein this means is disposed in optical alignment with and physically rearward of said analyzer means;
   h. means, in optical alignment with said analyzer means and physically disposed between said analyzer means and said means for permitting transmission of only a preselected constituent wavelength of said emitted beam of light, for shortening the geometric distance of an optical path between said analyzer means and said light transmitting means, wherein this means for shortening said geometric distance includes a third mirror physically disposed between said analyzer means and said light transmission means, such that light transmitted by said analyzer means impinges upon said third mirror and is reflected therefrom to said light transmission means;
   i. means for detecting the light and the intensity of the light transmitted by said means for permitting transmission of only a preselected constituent wavelength of said beam of light, wherein said light and light intensity detecting means includes a photodetector and is disposed in optical alignment with and physically rearward of said means for permitting transmission of only a preselected constituent wavelength of said beam of light;
   j. means for indicating if said intensity of said detected light exceeds a predetermined threshold of intensity of light, wherein this means includes a visual indicating means, and wherein this means is operatively associated with said means for detecting said light and said intensity of said light;
   k. a container common to, and housing, all of said foregoing components, wherein said container has a forward end in which is located an opening; and
   l. means, external of and connected to said container, for abutting said light-reflective surface and for permitting a spaced-apart relationship between said forward end of said container and said light-reflective surface, wherein this means includes at least two spaced-apart feet members connected to said forward end of said container, with at least one said foot member on one side of said container opening, and with at least another foot member on the other side of said container opening;

whereby, if said intensity of said detected light does exceed said predetermined threshold, then said light-reflective surface, which is being tested, is contaminated.

2. A hand-holdable contamination tester, as set forth in claim 1, wherein said container has ends of a width of two inches each and has sides therebetween of a length of five inches each.

* * * * *